United States Patent [19]

Schoellkopf et al.

[11] Patent Number: 5,138,071
[45] Date of Patent: Aug. 11, 1992

[54] PROCESS FOR PREPARING PEPTIDES WITH N-TERMINAL NON-PROTEINOGENOUS AMINO ACIDS

[75] Inventors: Ulrich Schoellkopf, Bovenden; Ulrich Groth, Goettingen, both of Fed. Rep. of Germany; Meinolf Lange, Lyndhurst, N.J.

[73] Assignee: BASF Aktiengesellschaft, Ludwigshafen, Fed. Rep. of Germany

[21] Appl. No.: 671,759

[22] PCT Filed: Sep. 9, 1989

[86] PCT No.: PCT/EP89/01051
§ 371 Date: Mar. 18, 1991
§ 102(e) Date: Mar. 18, 1991

[87] PCT Pub. No.: WO90/03387
PCT Pub. Date: Apr. 5, 1990

[30] Foreign Application Priority Data

Sep. 17, 1988 [DE] Fed. Rep. of Germany ....... 3831717

[51] Int. Cl.[5] ............... C07D 207/09; C07C 67/00; C07C 229/26
[52] U.S. Cl. .................. 548/537; 560/16; 560/39; 560/41; 560/125; 560/153; 560/169; 562/450; 562/561
[58] Field of Search ............. 560/16, 153, 39, 41, 560/169, 125; 548/537; 562/450, 561

[56] References Cited

U.S. PATENT DOCUMENTS 4,448,716  5/1984  Tsau ........................ 560/169
4,634,792  1/1987  Zanno et al. ............... 560/169

OTHER PUBLICATIONS

*Liebigs Annalen der Chemie*, Nr. 3, Mar. 1987, B. Kohler et al. pp. 267–269.
*Helvetica Chimica Acta*, vol. 69, (1986), Wipf et al., pp. 1153–1162.
*Journal of the American Chemical Society*, vol. 103, 1981, pp. 5991–7040, Balasubramanian, et al.

*Primary Examiner*—Jose G. Dees
*Assistant Examiner*—Vera C. Clarke
*Attorney, Agent, or Firm*—Oblon, Spivak, McClelland, Maier & Neustadt

[57] ABSTRACT

A process for preparing dipeptides with N-terminal non-proteinogenous amino acids of the formula

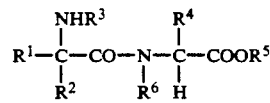

in which $R^1$ to $R^6$ have the meaning stated in the description, from compounds of the formula

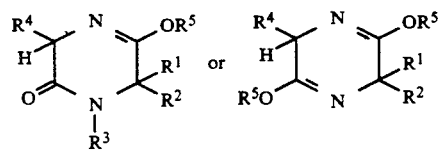

is described.

1 Claim, No Drawings

PROCESS FOR PREPARING PEPTIDES WITH N-TERMINAL NON-PROTEINOGENOUS AMINO ACIDS

DESCRIPTION

The present invention relates to a process for preparing dipeptides which are derived from non-proteinogenous amino acids.

The specific synthesis of peptides which contain non-proteinogenous amino acids employs the unnatural amino acids and uses conventional protective groups and activation methods for the stepwise synthesis of the required peptides.

The unnatural amino acids employed are in this strategy obtained either by a non-enantioselective synthesis and subsequent racemate resolution or by enantioselective syntheses using optically active auxiliaries.

Difficulties in the formation of the peptide linkage may occur especially when the α-position of the unnatural amino acid is substituted by two sterically demanding radicals (Helv. Chim. Acta 69, (1986) 1153, J. Amer. Chem. Soc. 103 (1981) 6127).

It has now been found that certain dipeptides can be prepared in a straightforward manner.

The invention relates to a process for preparing dipeptides with N-terminal non-proteinogenous amino acids of the formula I

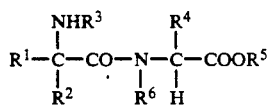

in which $R^1$ is a $C_1$-$C_8$-alkyl, phenyl or benzyl group, $R^2$ denotes a $C_1$-$C_8$-alkyl group which can be interrupted by —O—, —S—, —CO— or —CO—O—, or denotes a phenyl or benzyl group, $R^3$ is a hydrogen atom or represents, together with $R^2$, the radicals —(CH$_2$)$_3$—, —(CH$_2$)$_4$— or —CH$_2$—CH=CH—CH$_2$—, and $R^4$ denotes a methyl, isopropyl, isobutyl, 2-butyl, t-butyl or benzyl radical, $R^5$ represents a methyl or ethyl group, and $R^6$ represents a hydrogen atom or a $C_1$-$C_8$ -alkyl group, but where at least one of the two radicals $R^3$ or $R^6$ is a hydrogen atom, which comprises a) — if $R^6$ is a hydrogen atom — reacting a compound of the formula II

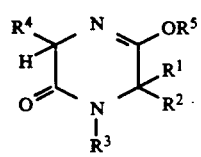

in which $R^1$ to $R^5$ have the stated meaning, with trialkyloxonium fluoroborate to give compounds of the formula III

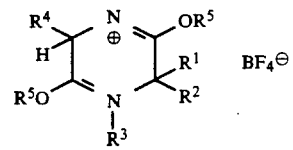

in which $R^1$ to $R^5$ have the stated meaning, and subjecting the compounds obtained in this way to acid cleavage and hydrolysis, or b) — if $R^3$ denotes a hydrogen atom and $R^5$ denotes an ethyl group — reacting a compound of the formula IV

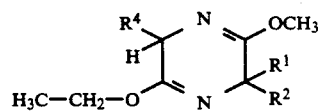

in which $R^1$, $R^2$ and $R^4$ have the stated meaning, with a trialkylsilyl iodide, then alkylating where appropriate and subsequently cleaving with acid the compounds obtained in this way, or c) — if $R^3$ is a hydrogen atom — treating a compound of the formula VIII

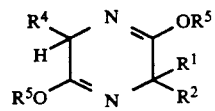

in which $R^1$-$R^5$ have the stated meaning, with acid.

The conversion of compounds II into I according to a) takes place in accordance with the following scheme:

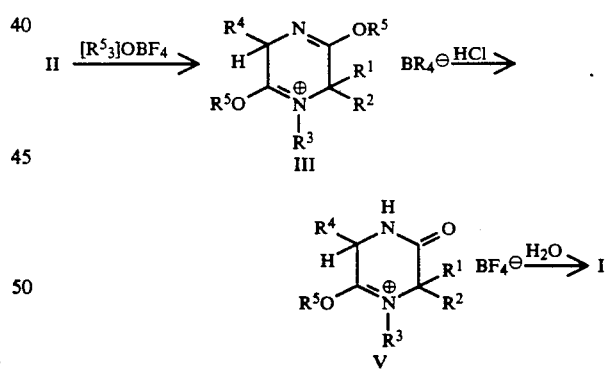

The alkylation of the monolactim ethers II is carried out with Meerwein salts, preferably triethyloxonium tetrafluoroborate or trimethyloxonium tetrafluoroborate in dichloromethane at room temperature. The reaction takes from 6 to 48 h.

The solution of the immonium salts III obtained in this way is saturated at temperatures from 0° to 30° C., preferably at room temperature with hydrogen chloride. After 5 min to 6 h have elapsed, water is added to the solution of V, which results at room temperature in compounds I. The hydrolysis is generally complete after 15 min to 6 h.

The compounds of the formula I in which $R^3$ is a hydrogen atom and $R^5$ is an ethyl group can be prepared especially well according to b) from compounds of the formula VI

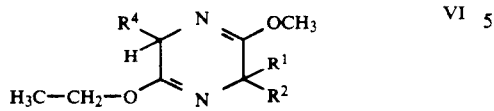

by reaction with a trialkylsilyl iodide, preferably with 1–8 C atoms in the alkyl radicals and, especially, with trimethylsilyl iodide. The reaction is expediently carried out at from 0° to −20° C. in an anhydrous halogenated hydrocarbon, preferably dichloromethane, as solvent.

The monolactim ethers obtained in this way, of the formula

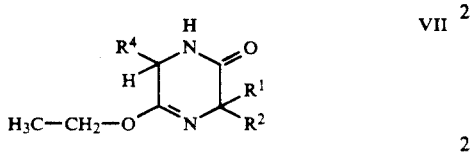

are subsequently hydrolyzed as described above to the compounds I.

The acid cleavage of the compounds VIII (process c) takes place via a compound of the formula

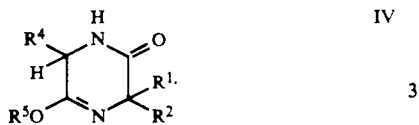

The cleavage is expediently carried out with hydrochloric acid at room temperature. If it is required to prepare substances of the formula I in which $R^6$ represents an alkyl radical, it is necessary to alkylate the substances IV on the nitrogen before the acid cleavage.

Since some of the compounds of the formula I in the form of the free bases readily form the corresponding diketopiperazines by ring closure, the salts of I resulting from the hydrolysis are preferably either converted into the N-protected derivatives by reaction with the acylating agents customary in peptide chemistry, such as benzoyloxycarbonyl chloride, fluorenyl-9-methoxycarbonyl chloride or di-tert-butyl carbonate (cf. Houben-Weyl, Methoden der organischen Chemie, Vol. 15/1, G. Thieme Verlag, Stuttgart 1974), or reacted with activated amino-acid derivatives (cf. Houben-Weyl, Methoden der organischen Chemie, Vol. 15/2, G. Thieme Verlag, Stuttgart 1974) to give tripeptide derivatives.

The compounds I have two asymmetric C atoms which may have the R and S configuration and whose configuration can be identical or different.

The starting materials required for the synthesis are mainly known, cf. Pure Appl. Chem 55, 1799 (1983), Angew. Chem. 99, 137 (1987).

The compounds VI can be prepared particularly straightforwardly by reacting a compound of the formula

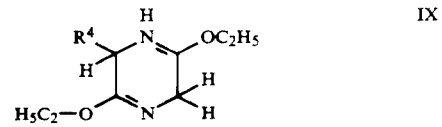

with a mono- or dialkylamine in the presence of a trialkyl borate or of another mild Lewis acid to give a compound of the formula

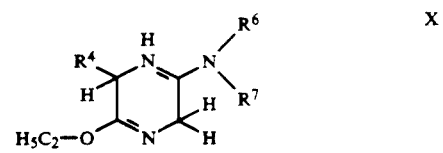

in which $R^6$ represents a hydrogen atom or a $C_1$–$C_6$-alkyl group and $R^7$ represents a $C_1$–$C_6$-alkyl group, removing the amine residue by hydrolysis and subsequently methylating the hydrolysis product in the six position with trimethyloxonium tetrafluoborate. The mixed bislactim ethers obtained in this way, of the formula

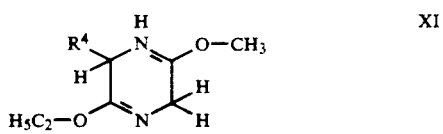

can subsequently be converted by single or double C-alkylation of their lithium salts into the intermediates VI.

The conversion of IX into X is preferably carried out by reacting IX with a methanolic solution of about 1.5 equivalents of mono- or dialkylamine in the presence of catalytic amounts of a Lewis acid at 20° to 60° C. The compounds X are purified by distillation.

The conversion of X into XI takes place in two steps. The amino group is eliminated in the first step by hydrolysis. For this, X is stirred in water at pH 6 to 9 at 50° to 100° C. Subsequently, extraction is carried out with a solvent such as halogenated hydrocarbon or ethyl acetate, and the resulting monolactim ether is alkylated with trimethyloxonium tetraborate. The alkylation is carried out in a chlorinated hydrocarbon at room temperature and usually takes from 1 to 3 days. Following the alkylation, the solution is neutralized and the compound XI is extracted.

The process according to the invention for preparing the α-alkyl-branched dipeptides is distinguished by the unnatural amino acid being synthesized on a lactim ether derivative, that is to say a masked dipeptide derivative, which can be obtained without difficulties. This chiral "auxiliary" II becomes part of the required dipeptide. The invention makes it possible to cleave selectively only one of the two intended fragmentation points in the compounds II. Surprisingly, selective hydrolysis at the amide linkage of II in the presence of an intrinsically more labile lactim ether group is possible by means of the stated reaction sequence.

Compounds of the formula I, and the N-protected derivatives which can be prepared therefrom in a straightforward manner by reaction with the customary acylating agents such as benzyloxycarbonyl chloride, fluorenyl-9-methoxycarbonyl chloride or di-tert-butyl dicarbonate ((BOC)₂O), are used as building blocks for synthesizing biologically active peptides. Thus, for example, a number of the tripeptides described in EP 99 056, which are suitable for the oral therapy of Parkinson's disease, can be obtained very satisfactorily by the process described above. Furthermore, the process is suitable for preparing building blocks for orally active peptides or peptide analogs which inhibit the enzyme renin and therefore can be employed for the therapy of high blood pressure.

EXAMPLE 1

R-αMePro-L-Val-OEt

A solution of 0.45 g of(2S,5R)-2,5-dihydro-2-isopropyl-6 -methoxy-5-methyl-pyrrolidino-pyrazin-3-one in dichloromethane was reacted with 0.76 g of triethyloxonium tetrafluoroborate while stirring at room temperature for 20 h. The mixture was subsequently saturated with HCl gas; after 1 h, 5 ml of water were added. The hydrolysis was complete after 2 h. For the working up, dichloromethane (30 ml) was added, and the pH was adjusted to 9 with ammonia. The aqueous phase was extracted with dichloromethane (2×10 ml). The organic extract was dried and evaporated in vacuo. Chromatography of the residue on silica gel (elution with dichloromethane/ether/ammonia 300:100:1) yielded 0.28 g (55%) of R-αMePro-L-Val-OEt.

EXAMPLE 2

R-αMePhe-L-Val-OEt 1.44 g of (2S,5R)-2,5-dihydro-2-isopropyl-3,6-dimethoxy-5-benzyl-5-methylpyrazine in 30 ml of diethyl ether were treated at room temperature with 25 ml of 0.2N HCl in diethyl ether. After 2 h, the mixture was evaporated in vacuo. Distillation of the residue gave 0.94 g (69%) of crude (2S,5R)-2,5-dihydro-2-isopropyl-6-methoxy-5-benzyl-methyl-pyrazin-3-one, boiling point 170° C./0.005 Torr.

(R)-αMePhe-L-Val-OEt was obtained in analogy to Example 1 from (2S,5R)-2,5-dihydro-2-isoprop-vl-1-methoxy-5-benzyl-5-methyl-pyrazin-3-one by reaction with triethyloxonium fluoborate and subsequent reaction with HCl/dichloromethane and hydrolysis.

We claim:

1. A process for preparing a dipeptide with an N-terminal non-proteinogenous amino acid of the formula I

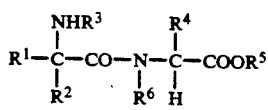

in which $R^1$ is a $C_1$–$C_8$-alkyl, phenyl or benzyl group,
$R^2$ denotes a $C_1$–$C_8$-alkyl, phenyl or benzyl group,
$R^3$ is a hydrogen atom or represents, together with $R^2$, the radicals —(CH₂)₃—, —(CH₂)₄—, or —CH₂—CH=CH—CH₂—, and
$R^4$ denotes a methyl, isopropyl, isobutyl, 2-butyl, t-butyl or benzyl radical,
$R^5$ represents a methyl or ethyl group, and
$R^6$ represents a hydrogen atom or a $C_1$–$C_8$-alkyl group, but where at least one of the two radicals $R^3$ or $R^4$ is a hydrogen atom, which comprises:

a) — if $R^6$ is a hydrogen atom — reacting a compound of the formula II

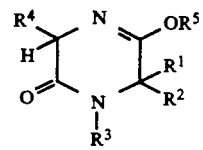

in which $R^1$ to $R^5$ have the stated meaning, with trialkyloxonioum fluoroborate to give a compound of the formula III

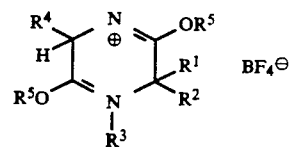

in which $R^1$ to $R^5$ have the stated meaning, and subjecting the compound obtained in this way to acid cleavage and hydrolysis, or b) — if $R^3$ denotes a hydrogen atom and $R^5$ denotes an ethyl group — reacting a compound of the formula IV

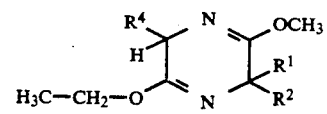

in which $R^1$, $R^2$ and $R^4$ have the stated meaning, with a trialkylsilyl iodide, then alkylating to introduce $R^6$ and subsequently cleaving with an acid the compound obtained in this way, or c) — if $R^3$ is a hydrogen atom — treating a compound of the formula VIII

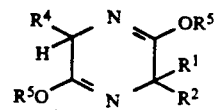

in which $R^1$–$R^5$ have the stated meaning, with an acid.

* * * * *

UNITED STATES PATENT AND TRADEMARK OFFICE
CERTIFICATE OF CORRECTION

PATENT NO. : 5,138,071

DATED : August 11, 1992

INVENTOR(S) : Ulrich Schoellkopf et al.

It is certified that error appears in the above-identified patent and that said Letters Patent is hereby corrected as shown below:

On the Title page, item [54] and Col. 1, line 1, the title should read

--PROCESS FOR PREPARING DIPEPTIDES WITH N-TERMINAL NON-PROTEINOGENOUS AMINO ACIDS--.

Signed and Sealed this

Tenth Day of August, 1993

*Attest:*

MICHAEL K. KIRK

*Attesting Officer*     *Acting Commissioner of Patents and Trademarks*